United States Patent [19]

Baillie

[11] Patent Number: 5,104,228

[45] Date of Patent: Apr. 14, 1992

[54] PHOTOSENSITIVE TURBIDIMETER WITH NONFOULING MEASUREMENT CHAMBER

[75] Inventor: Lloyd A. Baillie, Plano, Tex.

[73] Assignee: Atlantic Richfield Company, Los Angeles, Calif.

[21] Appl. No.: 585,420

[22] Filed: Sep. 20, 1990

[51] Int. Cl.⁵ .............................................. G01N 21/85
[52] U.S. Cl. .................................. 356/442; 356/440; 250/576; 73/61.1 R
[58] Field of Search ............... 356/441, 442, 436, 246, 356/70, 440; 73/61.1, 323, 324; 359/507, 509; 250/576

[56] References Cited

PUBLICATIONS

Derwent Abstract, 88.262592/37 (23.02.88).

Primary Examiner—Vincent P. McGraw
Assistant Examiner—LaCharles P. Keesee
Attorney, Agent, or Firm—Michael E. Martin

[57] ABSTRACT

The turbidity of liquids, including oil contaminated water, may be measured by an apparatus having a first elongated shell member defining a turbid liquid measurement chamber and opposed head members forming windows for transmitting a light beam through the measurement chamber between a light source and photosensitive element. A second shell member is disposed around the first shell member and defines with the first shell member and the opposed head members clear liquid supply chambers for supplying a clear liquid to wash over the windows and prevent contact of the turbid liquid with windows during operation of the apparatus. A flow of clear liquid, such as water, may be controlled by a pump and a throttling valve with orifices in each flow line to limit the flow of clear liquid. A mixture of clear liquid and turbid liquid is discharged from the turbidity measurement chamber into a discharge manifold formed between the shell members.

4 Claims, 1 Drawing Sheet

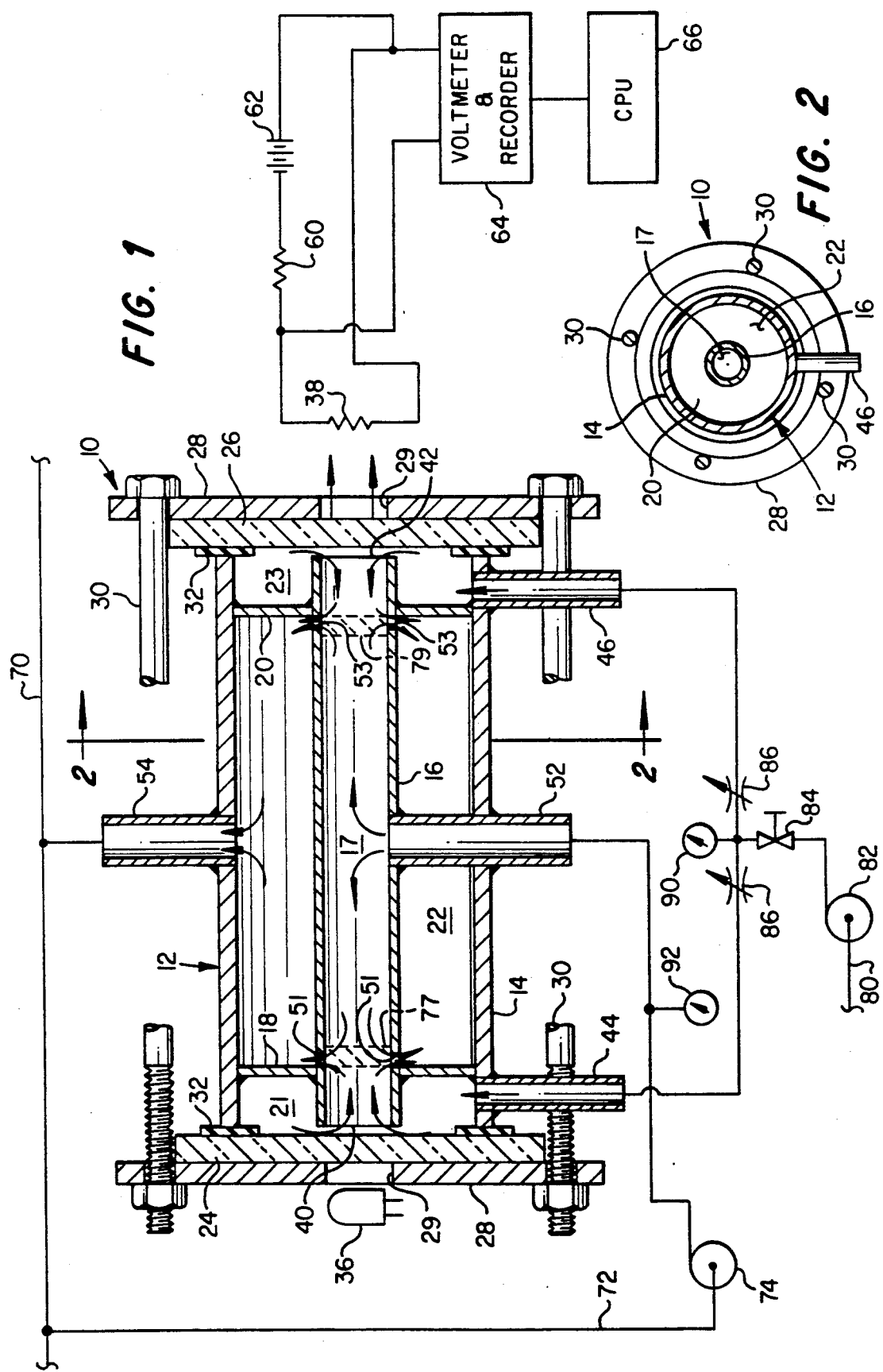

PHOTOSENSITIVE TURBIDIMETER WITH NONFOULING MEASUREMENT CHAMBER

BACKGROUND OF THE INVENTION

1. Field of the Invention

The present invention pertains to an apparatus for measuring the turbidity of a liquid, including measuring the presence of oil or other contaminants in water, wherein a windowed chamber is defined for measuring the change in the intensity of a light beam, and the chamber is arranged to prevent fouling of the windows by isolating the contaminated or turbid fluid stream from contact with the windows by clear fluid wash streams.

2. Background

My U.S Pat. No. 4,809,543, assigned to the assignee of the present invention, describes an apparatus for measuring the turbidity of a fluid stream, in particular for use in determining the concentration of oil and water. This apparatus has an arrangement wherein the turbid flowstream is directed into the interior of a vessel defining a turbidity chamber wherein a light source is beamed through the chamber by way of opposed windows and onto a photosensitive element such as a photoresister.

Although the apparatus provides for a superior method for determining the concentration of oil in water, or the turbidity of a fluid flowstream, certain fluids include impurities which are so adherent that accumulations occur on the windows, despite the turbulence caused by the arrangement of liquid jets which face the windows. Efforts to provide suitable window materials which do not become coated with liquid contaminants have heretofore been unsuccessful.

SUMMARY OF THE INVENTION

The present invention provides an improved apparatus for determining the turbidity of a liquid stream, in particular, the concentration of oil or other contaminants in a water stream. In accordance with one aspect of the present invention, an apparatus is provided wherein a chamber is defined by a vessel which has opposed light-transmitting windows formed therein and through which a light beam is transmitted to a photosensitive element. A sample of a liquid flowstream whose turbidity is to be measured is conducted through the chamber, and the changes in the light intensity as sensed by the photosensitive element are measured to determine the turbidity of the sample stream. In order to prevent fouling of the vessel windows, opposed streams of clear water are interposed between the vessel windows and the turbid liquid stream to prevent contact of the turbid liquid with the windows and so as to prevent fouling thereof. The clear water, which is continuously conducted across the vessel windows, mixes with the turbid or contaminated liquid and leaves the vessel through spaced-apart sets of orifices formed in the vessel. In this way, the contaminated liquid or the liquid stream whose turbidity is to be measured does not physically contact the vessel windows, and the windows remain clean to enhance the accuracy of measurement of the turbidity of the liquid stream.

The present invention further provides a unique photosensitive cell or vessel for a turbidimeter having an arrangement of concentric manifolds for conducting a turbid liquid flowstream and opposed clear liquid flowstreams through the vessel in such a way that the streams do not mix prior to contact with light-transmitting vessel windows, and the turbid flowstream is not permitted to contact the vessel windows.

Those skilled in the art will recognize the above-described features and superior aspects of the present invention, as well as other advantages thereof, upon reading the detailed description which follows in conjunction with the drawing.

BRIEF DESCRIPTION OF THE DRAWING

FIG. 1 is a somewhat schematic diagram of the improved turbidimeter of the present invention; and FIG. 2 is a section view taken along the line 2—2 of FIG. 1.

DESCRIPTION OF A PREFERRED EMBODIMENT

In the description which follows, like parts are marked throughout the specification and drawing with the same reference numerals, respectively. The drawing figures are not necessarily to scale, and certain features of the invention are shown in schematic form in the interest of clarity and conciseness.

Referring to FIG. 1, there is illustrated an improved turbidimeter in accordance with the present invention and generally designated by the numeral 10. The turbidimeter 10 includes a generally cylindrical vessel 12 having an outer cylindrical shell member 14 and a concentrically-spaced inner cylindrical shell member 16. The inner shell member 16 is supported with respect to the outer shell member 14 by spaced-apart transverse partitions 18 and 20, defining with the shell members a generally annular fluid discharge flow chamber 22. Opposite ends of the shell member 14 are closed by opposed transparent plastic or glass head members 24 and 26, which are supported in fluid-tight engagement with the shell member 14 by respective flanges 28 and spaced-apart, conventional bolt and nut assemblies 30. Suitable ring-shaped gaskets 32 are interposed between the head members 24 and 26 and the opposed end faces of the shell member 14, as illustrated. Each of the flanges 28 has a generally cylindrical central opening 29 formed therein to permit a light beam to pass through turbidity measurement chamber 17 defined by the inner, generally tubular shell member 16. A light source 36 is disposed adjacent one of the flanges 28 and a photosensitive element such a photoresister 38 is disposed adjacent the opposite flange 28, as illustrated. Accordingly, a light beam may pass through the clear windows formed by the head members 24 and 26 and the chamber 17. The intensity of the light beam transmitted from the source 36 to the photosensitive element 38 is determined by the turbidity of fluid in the chamber 17.

The partitions 18 and 20 define, respectively, with the respective head members 24 and 26 opposed chambers 21 and 23. As illustrated in FIG. 1, a space is formed between each of the opposed end faces 40 and 42 of the shell member 16 and the surfaces of the head members 24 and 26 facing the chambers 21 and 23, respectively. In this way, liquid entering the chambers 21 and 23 from opposed supply conduits 44 and 46 may flow along the surfaces of the head members forming the light-transmitting windows for the chamber 17 to continually bathe these surfaces to prevent contamination or clouding of the surfaces by adherence of foreign matter from the liquid whose turbidity is being measured. A liquid whose turbidity is to be measured is introduced into the chamber 17 through an inlet conduit 52. The turbid liquid flows toward the head members 24 and 26 but is met by the clear liquid from the chambers 21 and 23, and both liquids exit the chamber 17 through spaced apart ports 51 and 53 which open into the chamber 22. All liquid entering the apparatus 10 is discharged from the chamber 22 by way of a discharge conduit 54.

The photoresister 38 is in circuit with a fixed resistance 60, an electrical source 62 and a voltmeter and recorder 64. The voltmeter and recorder 64 is suitably connected to a central processing unit 66 in accordance with a procedure for determining the turbidity of a fluid stream described in U.S. Pat. No. 4,809,543, which is incorporated herein by reference.

The turbidimeter 10 is, in one preferred application, adapted to measure the turbidity of liquid being conducted through a pipeline 70. Liquid is withdrawn from the pipeline 70 by way of a conduit 72 and a pump 74, which is connected to the inlet conduit 52. A source of clear liquid such as clear water, not shown, is adapted to be connected by way of a conduit 80 to a pump 82, which discharges the clear water through a control valve 84 and respective conduits connected to the clear water inlet conduits 44 and 46. Adjustable orifices 86 may be interposed in the conduits leading to the inlet conduits 44 and 46, as illustrated, for balancing the flow of clear liquid to maintain the cleanliness of the windows formed by the heads 24 and 26. Pressures in the fluid streams being conducted to the apparatus 10 are suitably monitored by pressure-sensing means 90 and 92, respectively.

Turbid liquid introduced into the chamber 17 will be met by a liquid flowstream from the chambers 21 and 23 which, when suitable pressures are adjusted with respect to the different flowstreams, will permit clear liquid to flow from the chambers 21 and 23 into the chamber 17, meeting the turbid liquid and wherein both liquid flowstreams mix and exit the chamber 17 by way of the ports 51 and 53 in the shell 16. The mixed liquid then flows into the chamber 22 and through the discharge conduit 54 back to the pipeline 70.

In operation, the chambers 21 and 23 are continuously supplied with clean water by way of the pump 82 and the respective orificed inlet conduits 44 and 46. Turbid fluid whose turbidity is to be measured by the photosensitive element 38 is conducted by way of the pump 74 into the chamber 17 but does not contact the windows 24 and 26, thanks to the fluidstreams of clear liquid entering the chamber 17 from each end of the shell 16 by way of the spaces provided between the end faces 44 and 42 and the respective surfaces of the head members 24 and 26 which form the light-transmitting windows. The width of the aforementioned spaces may be adjusted by the thickness of the gaskets 32. The response of the photosensitive element 38 will depend on the amount of sample turbid liquid in the light path formed by the chamber 17 and the light source 36. Most of this path will be occupied by the sample liquid, regardless of the ratio of clean water flow to the sample liquid flow.

Mixing of the clean water and the sample liquid will occur in relatively narrow, somewhat planar zones or spaces 77 and 79 which are directly adjacent to the ports 51 and 53, respectively, and subject to the control of the ratio of clean water flow to the sample liquid flow. Total flow through the apparatus 10 may be controlled by the pressure supplied by the pumps 74 and 82 and, of course, the size of the ports 51 and 53. The system described above may be periodically calibrated by shutting off the pump 74 while maintaining the flow of clean water through the conduits 44 and 46, the chambers 21 and 23 and the chamber 17. Some of the flow will exit the chamber 17 through the ports 51 and 53, and the remaining clean water flow may exit the chamber through the inlet conduit 52 as long as the pressure supplied by the pump 82 exceeds the pipeline flow pressure 70. In this way, the continuing flow of clear water quickly flushes the sample liquid chamber and a comparison of the clean water signal provided by the photosensitive element 38 may be made with respect tot he signal generated in response to sensing the turbidity of the sample liquid being measured.

Conventional elements for the light source 36 and the elements of the photoresister circuit may be used in the system of the present invention. The head members 24 and 26 which provide the light-transmitting "windows" may be made of a suitable acrylic plastic or a clear fluorocarbon plastic or any light-transmitting material which is compatible with the fluids being tested. In other respects, conventional engineering materials may be used for the shells 14 and 16 and the other structural elements described above.

In a test apparatus developed to reduce the present invention to practice, a pump-supplied turbid liquid to the chamber 17 at a pressure of 10 psig and the ports 51 and 53 comprised four 0.0625 inch diameter holes to provide liquid flow out of the chamber 17 on the order of about 1.9 GPM. The portion of this flow which comprised clean water is determined by the size of the orifices 86 and the pressure of the pump 82. If the orifices 86 were set to be of an effective diameter of about 0.093 inches and there is a 4.0 psi differential across the orifices, the clear water flow will be about 0.68 GPM out of a total of 1.9 GPM, in other words about one-third of the total flow through the apparatus 10.

Although a preferred embodiment of a nonfouling turbidimeter has been described hereinabove, those skilled in the art will recognize that various substitutions and modifications may be made to the apparatus described without departing from the scope and spirit of the invention as recited in the appended claims.

What is claimed is:

1. An apparatus for determining the turbidity of a liquid flowstream comprising:

turbid liquid pump means adapted to be in communication with a source of turbid liquid and for discharging said turbid liquid to a discharge conduit;

means forming a turbidity measurement chamber, including an elongated first shell member, said first shell member including conduit means in communication with said discharge conduit for receiving turbid liquid within said turbidity measurement chamber;

opposed head members spaced apart from each other and defining with said first shell member said turbidity chamber, said opposed head members including window means therein for transmitting a light beam therethrough and through said turbidity measurement chamber;

said head members each being spaced from opposite ends of said first shell member to define a liquid flow path across said window means, respectively;

means for introducing a clear liquid between said head members at said window means and said turbidity measurement chamber for causing a flow of clear liquid across the face of each of said window means and into said turbidity measurement chamber to prevent contact of said turbid liquid with said window means; and means forming fluid discharge ports in said first shell member for discharging said clear liquid and said turbid liquid from said turbidity measurement chamber.

2. The apparatus set forth in claim 1 including:

means forming another shell member disposed around said first shell member and defining a liquid discharge chamber for receiving a flow of turbid liquid and clear liquid from said turbidity measurement chamber.

3. The apparatus set forth in claim 2 wherein: said means forming said discharge chamber includes spaced apart partition means disposed between said first and said another shell members and defining clear liquid supply chambers for supplying clear liquid to be interposed between said window means and said turbid liquid, respectively.

4. The apparatus set forth in claim 1 including:

clear liquid pump means for pumping said clear liquid to said turbidity measurement chamber and flow control means interposed between said clear liquid pump means and said turbidity measurement chamber for controlling the flow of said clear liquid to be interposed between said window means and said turbid liquid.

* * * * *